United States Patent [19]

Söder et al.

[11] Patent Number: 4,755,470
[45] Date of Patent: Jul. 5, 1988

[54] PROCESS AND AN APPARATUS FOR MEASURING THE RELATIVE EQUILIBRIUM MOISTURE CONTENT

[75] Inventors: Jörg M. Söder, Cologne; Saleman Hamed, Leichlingen, both of Fed. Rep. of Germany

[73] Assignee: Agfa Gevaert Aktiengesellschaft, Leverkusen-Bayerwerk, Fed. Rep. of Germany

[21] Appl. No.: 807,964

[22] Filed: Dec. 12, 1985

[30] Foreign Application Priority Data

Dec. 22, 1984 [DE] Fed. Rep. of Germany ....... 3447214

[51] Int. Cl.$^4$ ...................... G01N 27/28; G01N 27/42
[52] U.S. Cl. ......................................... 436/39; 422/68; 422/102; 422/104; 422/90; 436/151; 436/155
[58] Field of Search ............ 422/102, 104, 58, 84–88, 422/68, 90; 436/39, 177, 181; 155; 73/73; 34/147, 24, 239; 138/104

[56] References Cited

U.S. PATENT DOCUMENTS

| | | | |
|---|---|---|---|
| 1,826,115 | 10/1931 | Ziebarth | 73/335 |
| 2,591,691 | 4/1952 | Forrester | 422/84 |
| 3,437,448 | 4/1969 | Miczka | 422/85 |
| 3,618,368 | 11/1971 | Lesemann | 73/73 |
| 3,671,195 | 6/1972 | Bersin | 422/104 |
| 3,775,229 | 11/1973 | Beckers | 34/239 |
| 4,227,399 | 10/1980 | Gröinger | 73/73 |

FOREIGN PATENT DOCUMENTS

| | | | |
|---|---|---|---|
| 0126599 | 10/1979 | Japan | 436/155 |
| 0019549 | 2/1983 | Japan | 73/73 |
| 0037552 | 3/1983 | Japan | 73/73 |

*Primary Examiner*—Michael S. Marcus
*Attorney, Agent, or Firm*—Connolly and Hutz

[57] ABSTRACT

A process for measuring the relative equilibrium moisture content, particularly of surface samples such as papers, films, woven material or the like, with which the sample is introduced into a hermetically sealable measuring tube and then the equilibrium moisture content arising from a temperature which is predetermined and adjustable by means of a thermostat is measured by a moisture sensor inserted into the measuring tube and not touching the sample. An apparatus serves to carry out the process which has a measuring tube which can be sealed on both sides and can be inserted into a thermostat, in which measuring tube frames are arranged for holding the sample to be examined, and which has a moisture sensor provided at the side sealing the measuring tube.

7 Claims, 1 Drawing Sheet

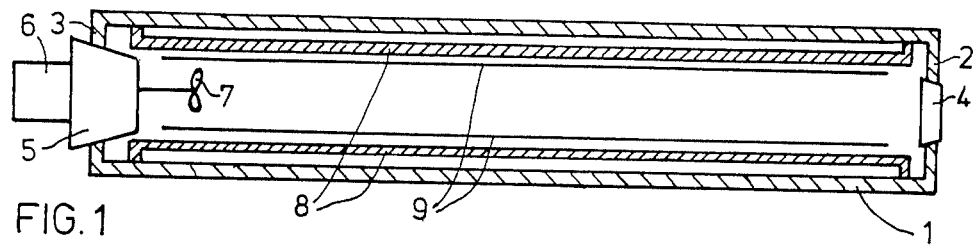
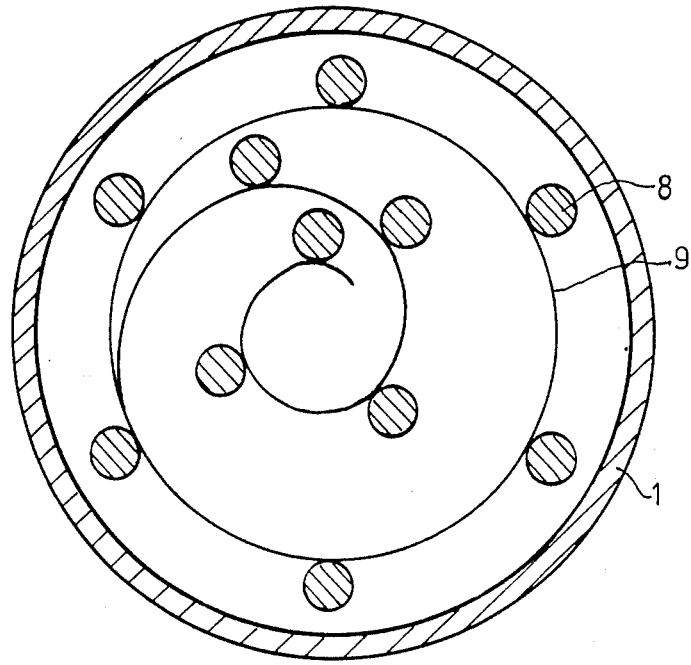
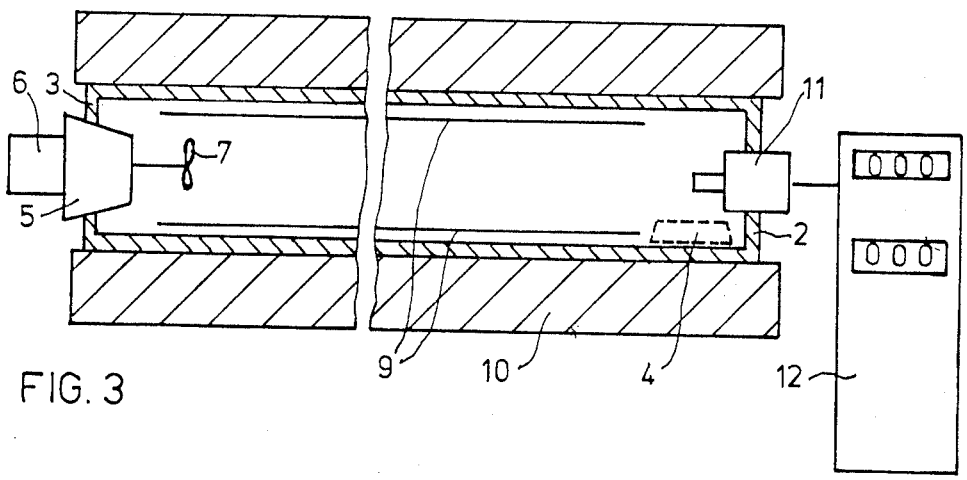

PROCESS AND AN APPARATUS FOR MEASURING THE RELATIVE EQUILIBRIUM MOISTURE CONTENT

This invention relates to a process for measuring the relative equilibrium moisture content, particularly of surface samples such as papers, films, woven material. The invention furthermore relates to an apparatus for carrying out the measuring process.

BACKGROUND

The relative equilibrium moisture content of the material often plays a substantial role in the further processing of material widths. In many cases it is sufficient if the equilibrium moisture content is examined in batch quantities by taking samples. For this purpose, commercial moisture measuring devices are offered on the market which operate by a so-called cap sensor. For measuring, the sensor is placed on the material. After a period of adjustment, an equilibrium moisture content is established in the occluded volume of the measuring chamber of the cap sensor and is representative of the product. The surface of the product contributing to the measurement is normally of the order of magnitude of 50 cm².

This measuring process is only suitable in the first place for measuring objects with smooth surfaces. In the case of objects with uneven surfaces, the cap sensor does not make flush contact with the surface, thus causing systematic measuring errors. A further source of error in this process is that with very thin material samples, the total available water quantity is not sufficient to produce an equilibrium state in the measuring volume defined by the cap sensor and the measuring cell, without the water content of the sample notably increasing or decreasing. Moreover, the problem exists with this process of sealing the sensor against external air which is produced by the cap sensor being pressed with its own weight onto the sample. Apart from this, fluctuations in temperature also have a damaging influence on the accuracy of the measurement. It is thus to be aimed for that the measurement of the relative equilibrium moisture content of the material sample takes place in a sealed system where disturbances by the surrounding air (air moisture and temperature) can be avoided.

SUMMARY OF THE INVENTION

This is where the invention comes into play. The object is to produce a measuring process for determining the relative equilibrium moisture content of material widths, which delivers good reproducible measuring values even under changing atmospheric conditions and is simple and safe with regards to handling.

This object is achieved according to the invention in that the surface material sample is introduced into a hermetically sealable measuring tube and then the equilibrium moisture content arising from a temperature which is predetermined and adjustable by means of a thermostat is measured by a moisture sensor inserted into the measuring tube and not touching the sample.

The air sealed in the measuring tube is advantageously circulated during measuring.

A measuring system designed according to this principle can also be easily calibrated. For this purpose, metal dishes with standard salt solutions with known steam pressures are inserted into the empty measuring tube.

A measuring device which is particularly suitable for carrying out the process is characterised by a measuring tube which can be sealed from both sides and can be inserted into a thermostat, in which measuring tube frames are arranged for holding the sample to be examined, and by a moisture sensor applied at the side sealing the measuring tube.

The frames are preferably arranged inside the measuring tube in such a manner that the surface sample to be examined is rolled in a spiral manner without the individual layers touching each other.

A flange or a stopper with a ventilator is advantageously arranged for the air circulation on the side of the measuring tube positioned opposite the moisture sensor.

The following advantages are achieved with the invention:

It has been shown that the relative moisture of the air originally present in the measuring tube plays practically no role, even with very thin material widths. The water absorption of the moisture sensor also has no influence on the accuracy of the measurement, that is its water absorption is negligible in relation to the water content of the measuring tube air. It has furthermore been shown that the moisture equilibrium in the measuring tube is established in a substantially shorter time when the air is circulated in the measuring tube by a small ventilator. In this manner the measuring time can be shortened.

An important advantage compared with the cap sensors known so far is that a substantially larger sample surface can contribute to the measuring without the air volume having to be correspondingly increased.

The measuring can be carried out at constant adjustable temperatures owing to the thermostatization. Disturbances by the surrounding atmosphere can be practically ruled out.

In the case of moisture measurement on photographic films and papers, the measures and movements necessary for the preparation and execution of the measuring must take place in the dark. The new measuring process is thereby substantially simpler since the sample only has to be inserted into the measuring tube and for determining the relative equilibrium moisture content can be placed in any other surrounding, e.g. in a daylight room.

BRIEF DESCRIPTION OF THE DRAWINGS

The invention is described in more detail below by means of an embodiment represented in the drawing.

FIG. 1 shows a sketch of the measuring tube with a sample inserted.

FIG. 2 shows a cross section through the measuring tube and

FIG. 3 shows a plan of the complete measuring phase.

DETAILED DESCRIPTION OF PREFERRED EMBODIMENT

The measuring tube according to FIG. 1 consists of a cylindrical metal tube 1 with side walls 2 and 3. In the side walls 2 and 3 are orifices which can be sealed by stoppers 4 and 5. On the stopper 5, a motor 6 is provided outside tube 1 and a ventilator 7 inside tube 1 driven by said motor for air circulation in the measuring tube. Inside the measuring tube, frames 8 are provided in a longitudinal direction which serve to hold a material sample, for example a film sample 9.

It can be seen from FIG. 2 that the longitudinal frames 8 are arranged on different radii in such a manner that the film sample 9 is held in a spiral manner. In this manner, it ensured that the total surface of the film sample is freely exchangable with the air surrounding it. It is thus prevented that the individual turns of the sample are mutually overlapped and/or part of the sample surface lies on the inside wall of the measuring tube.

The complete measuring phase and the course of the measuring process are explained below by means of FIG. 3. The measuring tube 1 with the sample 9 is here placed in a cylindrical automatic device 10 for regulating temperature. With the automatic device 10, each desired temperature between 10° and 30° C. can be established in the measuring tube 1. In place of the sealing stopper 4, a moisture sensor 11 is now used together with a temperature sensor. The two sensors are connected to a measuring amplifier 12 with a visual output for the temperature and the relative equilibrium moisture content.

The moisture sensor 11 here consists of a commercial measuring cell with a hygroscopic electrolyte based on LiCl/LiBr or a measuring cell with a polymer film. Measuring sensors of a different type can, however, also be used, for example dew point hygrometers.

For calibrating the measuring system, small metal dishes with different saturated standard salt solutions are inserted into the empty measuring tube. With each of these salt solutions, a defined known relative air moisture is produced in the measuring tube, the value of which can be obtained, for example, from the tables of the National Bureaus of Standard. By suitably selecting the standard salt solutions, the moisture range of interest can be sufficiently covered in each case.

The measurement of the equilibrium moisture content is carried out in such a manner that a film sample is taken from the batch to be examined and is inserted according to FIG. 2 into the measuring tube 1 in a rolled-together state. The measuring tube 1 with the conically formed stopper 5 is then hermetically sealed and transported to the measuring phase. The measuring tube 1 is there pushed into the automatic device 10 in order to bring the sample 9 to the desired measuring temperature.

Whereas the side 3 of the measuring tube 1 is sealed from the outside by the stopper 5, the opposite side 2 with the likewise conically formed stopper 4 is sealed from the inside. On introduction into the measuring phase, this stopper 4 is now pressed according to FIG. 3 into the measuring tube 1 and the orifice in the side wall 2 is sealed by the moisture/temperature sensor 11. It is thereby ensured that the air exchange with external air is kept to a minimum.

Naturally, the moisture/temperature sensor 11 can also be securely arranged on the front wall 2. It is then connected to the measuring amplifier 12 after inserting the measuring tube 1 into the automatic device 10.

During measuring an equilibrium moisture content is established inside the measuring tube at a constant temperature and is representative of the material moisture. In a typical measuring apparatus of this type, there is about 1 g of air in a measuring tube with a volume of 1 l, which air can absorb up to 20 mg of steam depending on the relative moisture. Electrolyte sensors with a diameter of the measuring cell of 0.7 mm with a thickness of from 1 to 2 $\mu$m absorb, according to experience, up to 0.01 mg of water. The water absorption of the measuring cell can thus be ignored in relation to the water content of the measuring tube air. The size of a film sample is typically 0.3 m$^2$. With a film casting thickness of 1 $\mu$m, up to 200 mg of water are present depending on the relative moisture. The water of the base is also added to this which, depending on the material, is at least of the same order of magnitude.

We claim:

1. A process for measuring the relative equilibrium moisture content of a sample in a sealed tube
   comprising the steps of
   introducing a sample into a tubular member having at least two orifices, a first orifice being sealed by a removable element positionable in said first orifice from within the tubular member, said sample being inserted through a second of said orifices,
   hermetically sealing said second orifice by a stopper
   then placing the tubular member into a thermostat,
   next forcing the removable element inward of the tubular member from the first orifice by the insertion into the first orifice of a moisture sensor,
   resealing the first orifice with the moisture sensor so constructed and arranged that the sensor and the sample are not contiguous,
   and at a selected temperature determined by said thermostat measuring the equilibrium moisture content of the sample.

2. A process according to claim 1, wherein air sealed in the measuring tubular member is circulated during measuring by a small ventilator.

3. A process according to claim 1, wherein the measuring system is calibrated prior to sample introduction by means of standard salt solutions.

4. In a combination for measuring the relative equilibrium moisture content of a sample,
   a tubular envelope having a pair of side walls intersecting an axis of the envelope,
   an orifice in each of said side walls,
   a removable element positionable in a first orifice in one of said side walls so constructed and arranged as to be insertable from within the envelope and to provide a seal with the envelope,
   a stopper positionable in a second orifice in another of said side walls so constructed and arranged as to be insertable from an exterior of the envelope and to provide a seal with the envelope,
   a moisture sensor insertable in said first orifice from an exterior of the envelope so constructed and arranged as to form a seal with the envelope
   whereby the sensor replaces the removable element
   and frames longitudinally positioned within envelope so constructed and arranged as to be capable of supporting a sample out of contact with said sensor in sealed position.

5. A combination according to claim 4, wherein the frames (1) inside the envelope (1) are positioned such that a surface sample to be examined is rolled in a spiral manner without individual layers touching each other.

6. In the combination as claimed in claim 4
   a thermostat receiving said tubular envelope adapted to actuate said moisture sensor at a selected temperature to measure the relative equilibrium moisture content of a sample.

7. The apparatus according to claim 4 further including a ventilator connected to said externally mounted stopper in said second orifice and positionable within said tubular envelope for air circulation.

* * * * *